US00PP09228P

United States Patent [19]

Trees

[11] Patent Number: Plant 9,228

[45] Date of Patent: Aug. 1, 1995

[54] GERANIUM PLANT NAMED BFP-445 SALMON

[75] Inventor: Scott C. Trees, Arroyo Grande, Calif.

[73] Assignee: Geo. J. Ball, Inc., West Chicago, Ill.

[21] Appl. No.: 341,911

[22] Filed: Nov. 15, 1994

[51] Int. Cl.[6] ..... A01H 5/00

[52] U.S. Cl. ..... Plt./87.12

[58] Field of Search ..... Plt. 87.12

[56] References Cited

U.S. PATENT DOCUMENTS

P.P. 8,296 7/1993 Trees ..... Plt./87.12

*Primary Examiner*—James R. Feyrer

*Attorney, Agent, or Firm*—Burns, Doane, Swecker & Mathis

[57] ABSTRACT

The new and distinct *Pelargonium*×*hortorum* cultivar named BFP-445 Salmon is provided. This new Zonal Geranium was the result of a controlled breeding program wherein the BSR-100B Dark Salmon cultivar (U.S. Plant Pat. No. 8,296) was pollinated by a plant designated 907-4. The new cultivar forms attractive medium salmon semi-double florets. Dark green foliage is well retained during shipment. The growth habit is medium self-branching and does not require the use of a growth regulator.

1 Drawing Sheet

SUMMARY OF THE INVENTION

The present invention comprises a new and distinct Geranium cultivar, botanically known as *Pelargonium*-×*hortorum* Bailey, and hereinafter is referred to by the cultivar name BFP-445 Salmon.

The new cultivar is a product of a planned breeding program which had the objective of the creation of a Geranium cultivar that exhibits uniform flowers, medium green foliage, a medium self-branching growth habit that requires no growth regulator, a propensity for rapid rooting, and stable foliage coloration during shipment.

The breeding program that resulted in the production of the new cultivar of the present invention was carried out in a controlled environment during 1989 at Arroyo Grande, Calif., U.S.A. The female parent (i.e., seed parent) was the BSR-100B Dark Salmon cultivar (U.S. Plant Pat. No. 8,296) which exhibits semi-double dark salmon florets with dark green foliage. The male parent (i.e., pollen parent) was a plant designated 907-4 (non-patented in the United States) which exhibits semi-double red florets with medium green foliage. The parentage of the new BFP-445 Salmon cultivar can be summarized as follows:

BSR-100B Dark Salmon×907-4.

BFP-445 Salmon was discovered and selected during 1990 as a highly distinctive flowering plant from among the progeny of the stated cross at Arroyo Grande, Calif., U.S.A. This plant was initially designated BFP-445.

It was found that the new cultivar of the present invention:

(a) exhibits attractive medium salmon semi-double florets,
(b) forms attractive dark green foliage with zonation, and
(c) exhibits a medium self-branching growth habit.

When plant material of the BFP-445 Salmon cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of BFP-445 Salmon cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1990 has demonstrated that the combination of unique characteristics as herein described for the BFP-445 Salmon cultivar is fixed and is retained through successive generations of such reproduction.

The new BFP-445 Salmon cultivar has not been observed under all possible environmental conditions. Accordingly, the described phenotype may vary somewhat with variations in the environment, such as temperature, light intensity, and day length.

Of the many commercial cultivars, the Eclipse Light Salmon cultivar (U.S. Plant Pat. No. 7,926) is considered to be the most similar to the new cultivar of the present invention. When the new cultivar of the present invention is compared to the Eclipse Light Salmon cultivar, it is found that the BFP-445 Salmon cultivar exhibits a distinctly darker floret coloration, larger florets (e.g., approximately 5.1 to 5.5 cm. vs. approximately 4.7 to 5.0 cm.) and fewer florets per umbel (e.g., approximately 25 to 35 vs. approximately 35 to 45). The BFP-446 Salmon cultivar additionally exhibits smaller umbels, shorter pedicel lengths, and longer internode lengths as specified in greater detail hereafter.

The new cultivar of the present invention is being marketed by Geo. J. Ball, Inc. under the Showcase trademark.

BRIEF DESCRIPTION OF THE PHOTOGRAPHS

The accompanying photographs show typical flower and foliage characteristics of the new BFP-445 Salmon cultivar with colors being as nearly true as it is reasonably possible to make the same in color illustrations of this character. The plants were being grown in greenhouses at West Chicago, Ill., U.S.A.

FIG. 1—illustrates the general appearance of an overall plant as seen primarily from above.

FIG. 2—illustrates the general appearance of another plant wherein the attractive zonation of the foliage is apparent.

DETAILED DESCRIPTION

Figure 1:
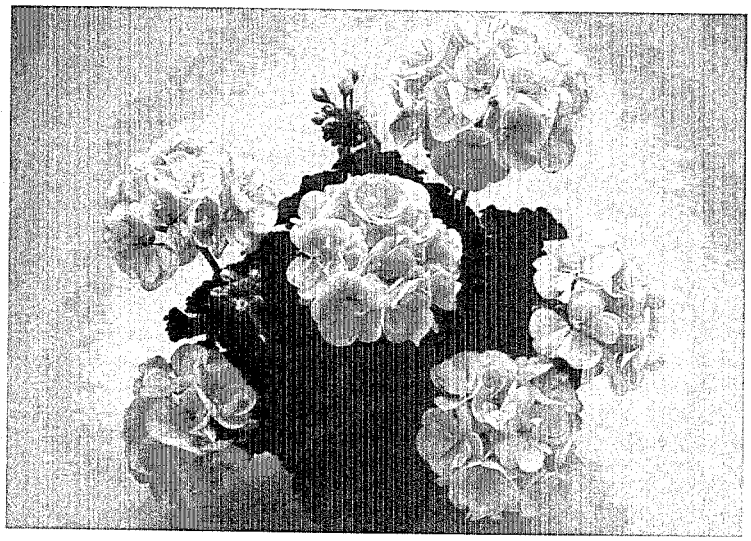
Figure 2:
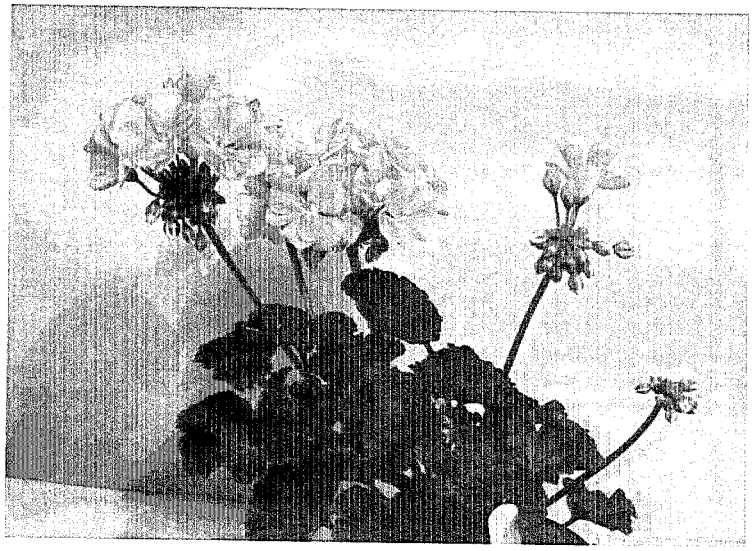

The following observations, measurements and comparisons describe plants grown in Ball FloraPlant's greenhouses located at West Chicago, Ill., U.S.A., under conditions which approximate those generally used in commercial practice. In the following description, color references are made to the R.H.S. Colour Chart of The Royal Horticultural Society, London, England. The color values were determined between 9:00 and 10:00 a.m. in Jul. 21, 1994, under natural light conditions of 2,000 footcandles.

Classification:

*Botanical.*—*Pelargonium*×*hortorum* Bailey, cv. BFP-445 Salmon.

*Commercial.*—Zonal Geranium.

INFLORESCENCE

A. Umbel:

*Average diameter.*—Approximately 9 to 10 cm. compared to approximately 12 to 13 cm. for the Eclipse Light Salmon cultivar.

*Average depth.*—Approximately 6 to 7 cm. compared to approximately 8 to 9 cm. for the Eclipse Light Salmon cultivar.

*Peduncle length.*—Approximately 14 to 17 cm. compared to approximately 16 to 17 cm. for the Eclipse Light Salmon cultivar.

*Pedicel length.*—Approximately 2.5 to 3.0 cm. compared to approximately 4.0 to 4.4 cm. for the Eclipse Light Salmon cultivar.

*Number of umbels plant.*—When grown in a 10 cm. pot at 9 weeks after the sticking of a rooted cutting, there commonly are approximately 7 to 8 umbels per plant. The Eclipse Light Salmon cultivar also commonly forms approximately 7 to 8 umbels per plant.

*Number of florets umbel.*—When grown in 10 cm. pots at 9 weeks, approximately 25 to 35 florets per umbel commonly are formed. This compares to approximately 35 to 45 umbels per plant for the Eclipse Light Salmon cultivar under the same growing conditions.

B. Corolla:

*Average diameter.*—Approximately 5.1 to 5.5 cm. compared to approximately 4.7 to 5.0 cm. for the Eclipse Light Salmon cultivar.

*Form.*—Both the BFP-445 Salmon cultivar and the Eclipse Light Salmon cultivar are semi-double.

*Number of petaloids.*—Commonly forms 2 to 3 petaloids per floret whereas the Eclipse Light Salmon cultivar only occasionally possesses 1 petaloid per floret.

*Color.*—General tonality from a distance of three meters: salmon. Adaxial: Red Group 43D. This compares to Red Group 49D for the Eclipse Light Salmon cultivar. Abaxial: Red Group 48C. This compares to Red Group 48C with veins of Red Group 56D for the Eclipse Light Salmon cultivar.

C. Bud:

*Shape.*—Oval-rounded.

*Color.*—Adaxial: Red Group 43D compared to Red Group 49D for the Eclipse Light Salmon cultivar. Abaxial: Red Group 48C for both.

D. Reproductive organs:

*Androecium.*—The anthers are commonly approximately 2 mm. in length. The pollen color is Orange-Red Group 33A. The filaments are approximately 4 to 6 mm. in length.

*Gynoecium.*—The pistil length commonly is approximately 8 to 9 mm. There is a single stigma which commonly has a length of approximately 4 mm. which commonly branches into 5 parts, and the style length is approximately 5 mm.

*Fertility.*—Usually does not produce fruits in the absence of mechanical fertilization.

E. Spring flowering response period: Approximately 6 to 7 weeks from rooted cuttings under greenhouse conditions.

F. Outdoor flower production: Freely flowering under outdoor growing conditions with substantially continuous blooming.

G. Durability: Ships well.

PLANT

A. Foliage: Dark green with zonation.

*Form.*—Reniform, with cordate base.

*Margin.*—Crenate.

*Color.*—Adaxial: Yellow-Green Group 147A at base and edges with a ring of Green Group 139A through the mid-section of the leaves. This compares to Yellow-Green Group 147A for the Eclipse Light Salmon cultivar. Abaxial: Yellow-Green Group 147B. This compares to Green Group 137C for the Eclipse Light Salmon cultivar.

*Size.*—Approximately 8 to 9 cm. at the widest point and approximately 6 to 7 cm. at the narrowest point. This compares to approximately 7.3 to 8.1 cm. at the widest point and approximately 6.1 to 7 cm. at the narrowest point for the Eclipse Light Salmon cultivar.

*Tolerance to botrytis.*—None claimed.

B. General appearance and form:

*Internode length.*—Commonly varies from approximately 2.0 to 2.45 cm. This compares to approximately 1.0 to 1.5 cm. for the Eclipse Light Salmon cultivar.

*Branching pattern.*—Freely basal branching. No pinching is required to obtain self-branching. A medium self-branching growth habit is observed in the absence of a growth regulator.

*Height.*—Approximately 28 to 32 cm. above a 10 cm. pot at 9 weeks under standard greenhouse conditions. This compares to approximately 25 to 28 cm. for the Eclipse Light Salmon cultivar.

I claim:

1. A new and distinct Geranium cultivar, substantially as herein shown and described, which:

(a) exhibits attractive medium salmon semi-double florets, (b) forms attractive dark green foliage with zonation, and (c) exhibits a medium self-branching growth.

* * * * *